United States Patent [19]

Parker

[11] 4,323,602

[45] Apr. 6, 1982

[54] WATER REPELLENT AND PRESERVATIVE FOR WOOD PRODUCTS

[75] Inventor: Thomas G. Parker, Three Rivers, Mich.

[73] Assignee: Roberts Consolidated Industries, Inc., City of Industries, Calif.

[21] Appl. No.: 149,155

[22] Filed: May 14, 1980

[51] Int. Cl.³ .................. B05D 1/18; B05D 1/28; B05D 3/00
[52] U.S. Cl. .................. 427/298; 106/18.29; 106/18.32; 106/18.35; 252/403; 252/405; 252/407; 427/351; 427/369; 427/429; 427/441; 428/485; 428/514; 260/28.5 R; 424/168; 424/173; 424/300; 424/81; 524/200
[58] Field of Search .......... 427/397, 396, 429, 298, 427/443, 429, 351, 369, 441; 252/280, 384, 344, 396, 403, 405, 407; 106/14, 15, 18.29, 18.32, 18.35; 424/300, 168, 173; 560/161; 428/485, 514; 260/28.5 R

[56] References Cited

U.S. PATENT DOCUMENTS

| 2,380,133 | 7/1945 | Waltmann et al. | 560/161 |
| 3,639,454 | 2/1972 | Richter | 560/161 |

FOREIGN PATENT DOCUMENTS

| 1203534 | 6/1962 | Fed. Rep. of Germany | 560/161 |
| 744134 | 7/1970 | France | 560/161 |

OTHER PUBLICATIONS

*Chemical Abstracts*, vol. 84, 1976, 84:43628n, p. 457.

*Primary Examiner*—Michael R. Lusignan
*Assistant Examiner*—Janyce A. Bell

[57] ABSTRACT

A combined water repellent and preservative for wood prepared in a concentrate for mixing with water and utilizing 3-iodo-2-propynyl butyl carbamate.

7 Claims, No Drawings

WATER REPELLENT AND PRESERVATIVE FOR WOOD PRODUCTS

BACKGROUND OF THE INVENTION

This invention relates to a water repellent and preservative for cellulose material such as wood, and in particular to an emulsion concentrate containing 3-iodo-2-propynyl butyl carbamate and designed for use by addition of water to provide an aqueous solution for impregnating the wood or other material.

Clean, penetrating, paintable solvent-based water repellent and preservatives for wood have been commercially available since the mid-1930's. These combined water repellent and preservatives are the most widely used products today for the protection of millwork items, shingles, siding, flooring, structural lumber, underlayment, sheathing, plywood, fences, outdoor furniture and other wood or wood-based products that must be protected from decay, staining organisms and wood destroying insects. These products are light-bodied, penetrating solutions that leave no perceptible surface coating, impart little or no color, are free from odor and make an excellent base for paint, varnish, enamel, stains, caulks and/or glazing compounds.

The water repellents reduce the natural affinity wood has for water. Wood splitting, end checking, and grain raising are minimized and service life of wood and finish is increased. Because of the penetrability of the product adequate protection can be obtained for above ground exposure, by brush application, flood coat, dip or long cold soak.

Although these organic solvent-based products have been successfully used for over 40 years their future is now in doubt. Clean air legislation will restrict and limit the use and discharge into the atmosphere of many solvents. Costs are escalating for solvents and freight. Insurance rates and fire hazards are greater when a flammable and combustible solvent is used. Pentachlorophenol, the principle fungicide used in current water repellent preservative formulations is undergoing review by the Environmental Protection Agency to determine if it should continue to be registered as a pesticide for treating wood. There is a need for a new generation of products that will eliminate the deficiencies of current solvent-based products yet retain the many desirable characteristics.

Accordingly, it is an object of the present invention to provide a new and improved water repellent preservative for wood which eliminates the undesirable features of the products currently in use. A further object is to provide such a material which can be used with various cellulose materials including paper, hardboard, particleboard, fiberboard, plywood, solid wood and some other materials.

Many preservative chemicals are effective when used alone, but are not compatible with other components that are needed to formulate a water repellent product which can be prepared in concentrate form and utilized by simple dilution with water to produce a ready-to-use aqueous solution.

It is a particular object of the present invention to provide a new and improved water repellent and preservative incorporating 3-iodo-2-propynyl butyl carbamate in an emulsion concentrate which can be diluted with water at the point of use to provide a ready-to-use water repellent preservative.

Desirable features of such material include: water based, requiring no organic solvents; stable both as a concentrate and after dilution in ready to use form; can be sold as a concentrate to save on storage and shipping costs; nonflammable both in the concentrate and ready to use form; low toxicity to animals and humans in both concentrate and ready to use form; effective in dimensionally stabilizing wood to minimize end checking, grain raising, splits, checks and other forms of degradation; contains a preservative effective to provide protection against staining and decay organisms and mildew and molds; results in a treated wood product which is paintable and receptive to adhesives, caulks and glazing compounds with no detrimental effect on color or appearance of applied finishes; vapors which are non-toxic and have low odor; biodegradeable but not chemically broken down when exposed to the sun, while having good heat resistance; and meets the performance requirements of Industrial Standard IS-4 (NWMA) and Federal Spec. TT-W-572B.

It is an object of the present invention to provide a new and improved material which has the features set out above.

Other objects, advantages, features and results will more fully appear in the course of the following description.

SUMMARY OF THE INVENTION

The present invention includes a method of protecting cellulose materials such as wood by impregnating the material with an aqueous solution containing 3-iodo-2-propynyl butyl carbamate.

The invention also includes a combined water repellent and preservative emulsion concentrate suitable for dilution in water and treatment of cellulose material such as wood by impregnating the wood with the diluted concentrate. The invention also includes the method of treating the cellulose material with the concentrate including the steps of diluting the concentrate and impregnating the wood with the resultant solution.

A particular feature of the invention is the production and use of a concentrate containing a water insoluble active ingredient 3-iodo-2-propynyl butyl carbamate dispersed in a latex and wax emulsion to produce a stable homogeneous concentrate which can be diluted with water at the point of use to provide the water repellent preservative for wood which can be applied by brush, flood spray, immersion, soak, vacuum, pressure or otherwise as desired.

DESCRIPTION OF THE PREFERRED EMBODIMENTS

Many preservative chemicals presently available are effective when used alone, but are not compatible with other materials that are needed in a finished product to provide a concentrate for use as a water repellent and preservative for wood or other cellulosic materials. The present invention utilizes as the active preservative, 3-iodo-2-propynyl butyl carbamate, incorporating this material in high concentration with water repellent material which after processing are readily dilutable with water to provide an easily applied water repellent preservative. Some raw materials in such a product tend to mask the effectiveness of the fungicide. In the present invention, the selection of raw materials and the sequence in which they are combined is important in producing an emulsion of water repellent and preservative ingredients resulting in a solution which is stable at low and high temperatures and over a broad range of pH with no separations.

The constituents and the range of each in percent by weight for the 1+4 concentrate are set out in Table 1.

TABLE 1

| | Ranges in % by Weight | |
|---|---|---|
| 1. | 7.5–25% | paraffin wax emulsion 45–55% solids |
| 2. | 10–30% | acrylic latex emulsion 50–60% solids |
| 3. | 5–15% | ethylene glycol |
| 4. | 3.5–12.5% | 3-iodo-2-propynyl butyl carbamate 40% active |
| 5. | 0.1–1.0% | ethoxylated octylphenol |
| 6. | 0.1–1.0% | heteropolysaccharide |
| 7. | 30.0–60% | water |

TABLE 2

| | Typical 1 + 4 concentrate formula in % by weight | |
|---|---|---|
| 1. | 15% | paraffin wax emulsion |
| 2. | 18.2% | acrylic latex emulsion |
| 3. | 8.0% | ethylene glycol |
| 4. | 6.1% | 3-iodo-2-propynyl butyl carbamate 40% active |
| 5. | 0.3% | ethoxylated octylphenol |
| 6. | 0.3% | heteropolysaccharide |
| 7. | 52.1% | water |

TABLE 3

| | Function of Ingredients |
|---|---|
| 1. | water repellent |
| 2. | vehicle and binder |
| 3. | freeze-thaw stabilizer and coupling agent |
| 4. | preservative |
| 5. | wetting agent and formula stabilizer |
| 6. | protective colloid and thickener |
| 7. | carrier |

Other suitable materials for the vehicle and binder (2) are polyvinyl acetate, vinyl acetate acrylic copolymer, and ethylene vinyl acetate. Other suitable materials for the stabilizers and coupling agent (3) are propylene glycol, and polyethylene glycol with a molecular weight range of 200–400. Other suitable materials for the thickener (6) are algin derivatives, guar gum derivatives, xanthan gum, hydroxy ethyl cellulose with a molecular weight range of 4,000–30,000, and carboxy vinyl polymer.

A typical formula in percent by weight to produce a concentrate suitable for dilution with the ratio of concentrate to water of 1+4 is set out in Table 2. For every one volume of concentrate, four volumes of water are added making five volumes of ready to use material. After mixing of concentrate and water, the material is applied to the wood by any of the conventional processes, including brushing, flood coating, dipping, long soak, and the like. While a 1+4 ratio of concentrate to water is presently preferred, concentrates may be produced for use with ratios of 1+1 to 1+6.

The functions of the various constituents are set out in Table 3.

The presently preferred procedure for producing the concentrate is set out in Table 4.

TABLE 4

| | Procedure |
|---|---|
| 1. | Add all of the water (7) to a first mixing vessel equipped with variable speed agitator. |
| 2. | Start agitation with sufficient speed so that a vortex develops. |
| 3. | Slowly sift the heteropolysaccharide (6) into the water and agitate for 15–30 minutes or until it is completely dispersed. |
| 4. | Add the acrylic latex emulsion (2). |
| 5. | Preblend the preservative (4), ethylene glycol (3) and ethoxylated octylphenol (5) in a second mixing vessel and agitate until a clear solution results. |
| 6. | Increase the agitation speed if necessary so a vortex is present but without splashing and slowly add the blend prepared in step 5 at rate of 3–6 gallons per minute. |
| 7. | Add the paraffin wax emulsion (1) slowly. |
| 8. | Mix for 10–15 minutes or until homogeneous. |

The procedure of Table 4 will yield a product having the following specifications:

| Concentration | - | 1 + 4 (dilutable with water) |
|---|---|---|
| Solids % | - | 30 ± 2 |
| pH | - | 5–7 |
| Wt/gal | - | 8.5–8.65 lbs. |
| Viscosity | - | 100–200 gm Brookfield RVT |
| Color | - | milk white to cream |
| Flashpoint | - | none |

A ready to use product is produced by adding four parts water to one part of the concentrate of Table 4, which has the following specification:

| pH | - 5–7 |
|---|---|
| Wt/gal | - 8.38 lbs. |
| Viscosity | - approximately same as water |
| Odor | - mild in solution, odor free when dry |
| Color | - milk white |
| Preservative | - 1.25% 3-iodo-2-propynyl butyl carbamate 40% active |

The ready to use product has the following characteristics in use:

| Water repellency - | swellometer test method 60%–80% |
|---|---|
| Penetration - | sapwood ponderosa pine 3-min. immersion ¼"–⅜" |
| Paintability - | Equal to untreated wood |
| Dry time at 72° F. | - 8–12 hrs. |
| Grain raising - | slight |
| Stability - | minimum of 1 year when stored in non-reactive containers and temperature 60°–80° F. |
| Corrosion - | compatible with substrates other than zinc, iron and steel |
| Leachability - | treated wood will not leach under wetting and drying conditions |

The product is freeze-thaw stable, non-flammable, easy to dilute at ambient conditions with a minimum of agitation, and stable in the dip tank after treating wood. The product does not introduce solvents in the system to cause wet back, nor discharge solvents on drying, and has low toxicity (Oral LD 50 1/10 Penta.). The product imparts little or no color change on wood, the treated wood has no residue odor, there is reduced penetration in blue stained or "sinker" stock, and the treated wood is non-corrosive. The product meets existing air pollution laws, is not hazardous to the environment, and produces no bloom.

The product of Table 2, diluted with four parts water, was tested as a fungicide using a standard National Woodwork Manufacturers Association (NWMA) Soil-Block Test to determine and compare effectiveness with a Standard Solvent Based 5% Penta treating solution. This test method is used to determine the minimum amount of preservative that is effective in preventing decay of selected species of wood by selected fungi under optimum laboratory conditions.

The test method may be briefly summarized as follows: Conditioned blocks of wood are impregnated with solutions of a preservative in water or organic solvent to form one or more series of gradient retentions of the preservative in the blocks. After periods of weathering, the impregnated blocks are exposed to the wood-destroying fungus, Lenzites trabea (Madison strain 617). The minimum amount of preservative which protects the impregnated blocks against decay by the fungus is defined as the threshold retention for that organism. Failure to protect is evidenced by loss of wood from the treated wood blocks, as indicated by a loss in weight.

The threshold retention expressed in pounds of treating solution per cubic foot of wood represents the minimum amount of preservative necessary to protect wood from decay. The threshold concentration is defined as the percent preservative in a given treating solution required to treat wood at a given retention to prevent decay. The use concentration as stipulated by the NWMA is 5.4 times the threshold concentration.

|  | Standard 5% Penta | Table 2, Diluted 1 + 4 |
|---|---|---|
| Threshold Retention | 0.192 lbs/ft$^3$ | 0.023 lbs/ft$^3$ |
| Threshold Concentration | 0.93% | 0.048% |
| Use Concentration | 5.02% | 0.27% |

The table 2 product when diluted 1+4 to the ready-to-use state contains 0.105 lbs 3-Iodo at 40% activity or 1.05×0.40=0.042 lbs. active 3-Iodo.

$$\frac{.042 \text{ lbs active}}{8.38 \text{ lbs/gal RTU}} \times 100 = .501\% \text{ active 3-Iodo in 1 gal RTU.}$$

NWMA requires 0.27% active 3-Iodo per gallon. Hence the ready-to-use water based Table 2 product contains (0.501/0.27) or 1.85 times more than the required amount.

Toxicity tests were conducted on the 1+4 concentrate of Table 2 with the following results:

ACUTE DERMAL LD 50:
Greater than 2.0 Ml/KG of body weight. In accordance with FHSA regulations, this material is not considered toxic by the dermal route of administration.

ACUTE INHALATION:
The test material, where aerosolized, produces particles of which 90% are greater than 100 microns in accordance with EPA guidelines, inhalation testing of this product is not required. (Materials which produce 80% or more particles greater than 10 microns in diameter does not require inhalation toxicity to support registration.)

AVIAN LD 50:
(Bobwhite Quail) is in excess of 2000 mg/kg of body weight.

DERMAL SENSITIZATION:
Based on the results obtained, this material is not considered as skin sensitizer.

ACUTE ORAL LD 50:
Greater than 5.0 Ml/KG of body weight for both male and female rats.

PRIMARY EYE IRRITATION:
0.0, not an eye irritant.

CHOLINESTERASE INHIBITION SCREEN:
The test sample (1+4 conc) 5 ml/kg of body weight caused significant decrease in the RBC cholinesterase activity in two hours after administration in male rats and in four hours after administration in female rats. The cholinesterase activity returned to normal within 24 hours after administration.

The test sample contained compounds that caused inhibition of cholinesterase activity of red blood cells.

DAPHNIA: (Aquatic invertebrate)

| Estimated LC 50: | 87 Mg/liter 95% confidence limits of 77 to 97 Mg/liter |
|---|---|

EPA TOXICITY CATEGORIES:
Category I—"Danger" or "Poison"; Category II—"Warning"; Category III—"CAUTION". Woodlife (Water Based) 1+4 concentrate based on EPA's outlined toxicity tests is classified as category III, 5% Penta based products are classified as category II.

Set out below as Tables 5, 6, 7 and 8 are usable concentrate formulas with the amount of one constituent varied. Constituent 1, the water repellent, is varied in Table 5; constituent 2, the vehicle and binder, is varied in Table 6; constituent 3, the stabilizer and coupling agent, is varied in Table 7; and constituent 4, the preservative is varied in Table 8. These tables show the useful ranges of the various constituents. The optimum values and the characteristics of the extremes are discussed in the notes following each table.

TABLE 5

WATER REPELLENT FORMULA RANGES IN % BY WEIGHT 1 + 4 CONCENTRATE AND RTU CONCENTRATION

| INGRE-DIENTS | #1 Conc. | #1 RTU | #2 Conc. | #2 RTU | #3 Conc. | #3 RTU | #4 Conc. | #4 RTU | #5 Conc. | #5 RTU | #6 Conc. | #6 RTU | #7 Conc. | #7 RTU |
|---|---|---|---|---|---|---|---|---|---|---|---|---|---|---|
| 1. Water Repellent | 3.75 | 0.75 | 5.0 | 1.0 | 6.25 | 1.25 | 7.5 | 1.5 | 10.0 | 2.0 | 12.5 | 2.5 | 15.0 | 3.0 |
| 2. Vehicle Binder | 10.0 | 2.00 | 10.0 | 2.00 | 10.0 | 2.00 | 10.0 | 2.00 | 10.0 | 2.00 | 10.0 | 2.00 | 10.0 | 2.00 |
| 3. Ethylene Glycol | 8.0 | 1.60 | 8.0 | 1.60 | 8.0 | 1.60 | 8.0 | 1.60 | 8.0 | 1.60 | 8.0 | 1.60 | 8.0 | 1.60 |
| 4. Preservative 40% | 6.1 | 1.22 | 6.1 | 1.22 | 6.1 | 1.22 | 6.1 | 1.22 | 6.1 | 1.22 | 6.1 | 1.22 | 6.1 | 1.22 |
| 5. Surfactant | 0.3 | 0.06 | 0.3 | 0.06 | 0.3 | 0.06 | 0.3 | 0.06 | 0.3 | 0.06 | 0.3 | 0.06 | 0.3 | 0.06 |
| 6. Protective Colloid | 0.3 | 0.06 | 0.3 | 0.06 | 0.3 | 0.06 | 0.3 | 0.06 | 0.3 | 0.06 | 0.3 | 0.03 | 0.3 | 0.06 |

TABLE 5-continued

WATER REPELLENT
FORMULA RANGES IN % BY WEIGHT 1 + 4 CONCENTRATE AND RTU

| INGRE- | #1 | | #2 | | #3 | | #4 | | #5 | | #6 | | #7 | |
|---|---|---|---|---|---|---|---|---|---|---|---|---|---|---|
| DIENTS | Conc. | RTU | Conc. | RTU | Conc. | RTU | Conc. | RTU | Conc. | RTU | Conc. | RTU | Conc. | RTU |
| 7. $H_2O$ | 71.55 | 94.31 | 70.3 | 94.06 | 54.6 | 90.92 | 67.8 | 93.56 | 65.3 | 93.06 | 62.8 | 92.56 | 60.3 | 92.06 |
|  | 100.00 | 100.00 | 100.00 | 100.00 | 100.00 | 100.00 | 100.00 | 100.00 | 100.00 | 100.00 | 100.00 | 100.00 | 100.00 | 100.00 |

Note;
Water repellent and vehicle binder listed as 100% solids in formulation. Above example show range of water repellent. All other ingredients at typical level.
Example #1 - Acceptable mix, however formula may not meet the 60% minimum requirements (swellometer method) under all conditions.
2 - Acceptable mix, again formula may not meet 60% minimum under all conditions.
3 - Acceptable mix, formula will meet the 60% minimum under all conditions.
4 - Typical formula, exceeds the 60% minimum requirements under all conditions.
5 - Acceptable mix, above optimum level, results improved durability and water repellency.
6 - Acceptable mix, again more durability and higher water repellency. Slower drying of paint may occur under some conditions.
7 - Acceptable mix, maximum level that can be used without severely altering the paintability. Paint may dry slower over wood treated with this formula, however, durability and water repellency would be excellent especially for wood that was not to be painted.

TABLE 6

VEHICLE BINDER
RANGES IN % BY WEIGHT FOR 1 + 4 CONC. AND RTU

CONCENTRATION

| INGRE- | #1 | | #2 | | #3 | | #4 | | #5 | | #6 | | #7 | |
|---|---|---|---|---|---|---|---|---|---|---|---|---|---|---|
| DIENTS | Conc. | RTU | Conc. | RTU | Conc. | RTU | Conc. | RTU | Conc. | RTU | Conc. | RTU | Conc. | RTU |
| 1. Water Repellent | 7.5 | 1.5 | 7.5 | 1.5 | 7.5 | 1.5 | 7.5 | 1.5 | 7.5 | 1.5 | 7.5 | 1.5 | 7.5 | 1.5 |
| 2. Vehicle Binder | 2.5 | 0.5 | 5.0 | 1.0 | 7.5 | 1.5 | 10.0 | 2.0 | 15.0 | 3.0 | 20.0 | 4.0 | 25.0 | 5.0 |
| 3. Ethylene Glycol | 8.0 | 1.6 | 8.0 | 1.6 | 8.0 | 1.6 | 8.0 | 1.6 | 8.0 | 1.6 | 8.0 | 1.6 | 8.0 | 1.6 |
| 4. Preservative 40% | 6.1 | 1.22 | 6.1 | 1.22 | 6.1 | 1.22 | 6.1 | 1.22 | 6.1 | 1.22 | 6.1 | 1.22 | 6.1 | 1.22 |
| 5. Surfactant | 0.3 | 0.06 | 0.3 | 0.06 | 0.3 | 0.06 | 0.3 | 0.06 | 0.3 | 0.06 | 0.3 | 0.06 | 0.3 | 0.06 |
| 6. Protective Colloid | 0.3 | 0.06 | 0.3 | 0.06 | 0.3 | 0.06 | 0.3 | 0.06 | 0.3 | 0.06 | 0.3 | 0.06 | 0.3 | 0.06 |
| 7. $H_2O$ | 75.3 | 95.06 | 72.8 | 94.56 | 70.3 | 94.06 | 67.8 | 93.56 | 62.8 | 92.56 | 57.8 | 91.56 | 52.8 | 90.56 |
|  | 100.00 | 100.00 | 100.00 | 100.00 | 100.00 | 100.00 | 100.00 | 100.00 | 100.00 | 100.00 | 100.00 | 100.00 | 100.00 | 100.00 |

Note:
Example show range of vehicle binder at 100% solids. All other ingredients at typical formula levels.
Example #1 - Acceptable mix, vehicle binder at minimum amount for durability and paintability.
2 - Acceptable mix, durability slightly improved, better dispersion of the preservative is realized.
3 - Acceptable mix, durability again improved.
4 - Typical formula, good durability and paintability, proper balance with other ingredients is realized.
5 - Acceptable mix, durability would be improved slightly.
6 - Acceptable mix, durability further increased, paintability is improved, penetration into wood may be slightly retarded.
7 - Acceptable mix, excellent durability would be realized, however vehicle binder at about the maximum amount that can be incorporated without changing the 1 + 4 concentration and still leave room for other ingredients.

TABLE 7

ETHYLENE GLYCOL
CONCENTRATION

| INGARE- | #1 | | #2 | | #3 | | #4 | | #5 | | #6 | | #7 | |
|---|---|---|---|---|---|---|---|---|---|---|---|---|---|---|
| DIENTS | Conc. | RTU | Conc. | RTU | Conc. | RTU | Conc. | RTU | Conc. | RTU | Conc. | RTU | Conc. | RTU |
| 1. Water Repellent | 7.5 | 1.5 | 7.5 | 1.5 | 7.5 | 1.5 | 7.5 | 1.5 | 7.5 | 1.5 | 7.5 | 1.5 | 7.5 | 1.5 |
| 2. Vehicle | 10.0 | 2.0 | 10.0 | 2.0 | 10.0 | 2.0 | 10.0 | 2.0 | 10.0 | 2.0 | 10.0 | 2.0 | 10.0 | 2.0 |
| 3. Ethylene Glycol | 2.0 | 0.4 | 4.0 | 0.8 | 6.0 | 1.2 | 8.0 | 1.6 | 10.0 | 2.0 | 15.0 | 3.0 | 20.0 | 4.0 |
| 4. Preservative 40% | 6.1 | 1.22 | 6.1 | 1.22 | 6.1 | 1.22 | 6.1 | 1.22 | 6.1 | 1.22 | 6.1 | 1.22 | 6.1 | 1.22 |
| 5. Surfactant | 0.3 | 0.06 | 0.3 | 0.06 | 0.3 | 0.06 | 0.3 | 0.06 | 0.3 | 0.06 | 0.3 | 0.06 | 0.3 | 0.06 |
| 6. Protective Colloid | 0.3 | 0.06 | 0.3 | 0.06 | 0.3 | 0.06 | 0.3 | 0.06 | 0.3 | 0.06 | 0.3 | 0.06 | 0.3 | 0.06 |
| 7. $H_2O$ | 73.8 | 94.76 | 71.8 | 94.36 | 69.8 | 93.96 | 67.8 | 93.56 | 65.8 | 93.16 | 60.8 | 92.16 | 55.8 | 91.16 |
|  | 100.00 | 100.00 | 100.00 | 100.00 | 100.00 | 100.00 | 100.00 | 100.00 | 100.00 | 100.00 | 100.00 | 100.00 | 100.00 |

Example #1 - Acceptable mix, however will not pass the required five-cycle freeze thaw at 0° F.
2 - Acceptable mix, will pass 1-2 cycles freeze thaw.
3 - Acceptable mix, will pass five cycles freeze thaw for the concentrate, however RTU is not freeze thaw stable.
4 - Acceptable mix, typical formula, will pass the required five-cycle freeze thaw for both concentrate and Ready-To-Use.
5 - Acceptable mix - freeze thaw would be further imporved.
6 - Acceptable mix, freeze thaw further improved, however amount not necessary for requirements that are met with #4.
7 - Acceptable mix, maximum amount that can be added without altering other desired properties such as paintability and water repellency.

TABLE 8

| | PRESERVATIVE RANGE IN % BY WEIGHT FOR 1 + 4 CONC. AND RTU CONCENTRATION | | | | | | | | | | | | | |
|---|---|---|---|---|---|---|---|---|---|---|---|---|---|---|
| INGRE- | #1 | | #2 | | #3 | | #4 | | #5 | | #6 | | #7 | |
| DIENTS | Conc. | RTU | Conc. | RTU | Conc. | RTU | Conc. | RTU | Conc. | RTU | Conc. | RTU | Conc. | RTU |
| 1. Water Repellent | 7.5 | 1.5 | 7.5 | 1.5 | 7.5 | 1.5 | 7.5 | 1.5 | 7.5 | 1.5 | 7.5 | 1.5 | 7.5 | 1.5 |
| 2. Vehicle | 10.0 | 2.0 | 10.0 | 2.0 | 10.0 | 2.0 | 10.0 | 2.0 | 10.0 | 2.0 | 10.0 | 2.0 | 10.0 | 2.0 |
| 3. Ethylene Glycol | 8.0 | 1.6 | 8.0 | 1.6 | 8.0 | 1.6 | 8.0 | 1.6 | 8.0 | 1.6 | 8.0 | 1.6 | 8.0 | 1.6 |
| 4. Preservative 40% | 0.625 | 0.125 | 1.25 | 0.25 | 3.4 | 0.68 | 6.1 | 1.22 | 9.4 | 1.88 | 12.5 | 2.5 | 15.6 | 3.13 |
| 5. Surfactant | 0.3 | 0.06 | 0.3 | 0.06 | 0.3 | 0.06 | 0.3 | 0.06 | 0.3 | 0.06 | 0.3 | 0.06 | 0.3 | 0.06 |
| 6. Protective Colloid | 0.3 | 0.06 | 0.3 | 0.06 | 0.3 | 0.06 | 0.3 | 0.06 | 0.3 | 0.06 | 0.3 | 0.06 | 0.3 | 0.06 |
| 7. H$_2$O | 73.375 | 94.655 | 72.65 | 94.53 | 70.5 | 94.10 | 67.8 | 93.56 | 74.5 | 92.90 | 61.4 | 92.28 | 58.3 | 91.66 |
| | 100.00 | 100.00 | 100.00 | 100.00 | 100.00 | 100.00 | 100.00 | 100.00 | 100.00 | 100.00 | 100.00 | 100.00 | 100.00 | 100.00 |

Note:
All preservative amounts must be multipled by 0.4 as the preservative is 40% active with the remainder an inert carrier.
Example
1 - Acceptable mix, preservative is at the threshold level where protection against decay is at the minimum point.
2 - Acceptable mix, preservative at twice the threshold level where it may be suitable for use under less severe conditions.
3 - Acceptable mix, preservative at 5.4 times the threshold level which is the requirement to meet industry standard.
4 - Typical formula, preservative at 10 times the threshold level for optimum performance under all conditions.
5 - Acceptable mix of preservative at 15 times the threshold level which is more than needed unless under very extreme conditions.
6 - Acceptable mix, preservative at 20 times the threshold level.
7 - Acceptable mix, preservative at 25 times threshold level. This is the maximum amount that can be incorporated and maintained in formula without altering the concentration or other ingredients. Only needed when exposure conditions are severe and wood species had little natural decay resistance.

I claim:

1. The method of protecting wood and wood based products by impregnating with an aqueous solution containing the fungicide 3-iodo-2-propynyl butyl carbamate.

2. The method of protecting wood and wood based products by impregnating with an aqueous solution containing 3-iodo-2-propynyl butyl carbamate and paraffin wax emulsion.

3. A combined water repellent and preservative emulsion concentrate for dilution with water and treatment of wood and wood based products comprising in percent by weight.

| | |
|---|---|
| 7.5–25% | paraffin wax emulsion 45–55% solids, |
| 10–30% | acrylic latex emulsion 50–60% solids, |
| 5–15% | ethylene glycol, |
| 3.5–12.5% | 3-iodo-2-propynyl butyl carbamate 40% active |
| 0.1–1.0% | ethoxylated octylphenol, |
| 0.1–1.0% | heteropolysaccharide, and |
| 30.0–60.0% | water. |

4. A combined water repellent and preservative emulsion concentrate for dilution with water and treatment of wood and wood based products comprising in percent by weight

| | |
|---|---|
| 15% | paraffin wax emulsion, |
| 18.2% | acrylic latex emulsion, |
| 8.0% | ethylene glycol, |
| 6.1% | 3-iodo-2-propynyl butyl carbamate 40% active, |
| 0.3% | ethoxylated octylphenol, |
| 0.3% | heteropolysaccharide, and |
| 52.1% | water. |

5. A combined water repellent and preservative emulsion concentrate for dilution with water and treatment of wood and wood based products comprising in percent by weight

| | |
|---|---|
| 7.5–25% | water repellent, |
| 10–30% | vehicle and binder, |
| 5–15% | freeze-thaw stabilizer and coupling agent, |
| 3.5–12.5% | 3-iodo-2-propynyl butyl carbamate, |
| 0.1–1.0% | wetting agent and stabilizer, |
| 0.1–1.0% | thickener, and |
| 30.0–60.0% | water. |

6. A combined water repellent and preservative emulsion concentrate for dilution with water and treatment of wood and wood based products comprising in combination water repellent, vehicle and binder, stabilizer and coupling agent, 3-iodo-2-propynyl butyl carbamate, wetting agent and stabilizer, thickener, and water.

7. The method of protecting wood and wood based products with the emulsion concentrate as defined in claim 3 including the steps of:
diluting the emulsion concentrate by mixing with water with the ratio of concentrate to water in the range of 1+1 to 1+6; and
impregnating the wood material with the diluted material.

* * * * *